United States Patent [19]
Roth et al.

[11] Patent Number: 6,037,361
[45] Date of Patent: Mar. 14, 2000

[54] FLUORINATED BUTYRIC ACIDS AND THEIR DERIVATIVES AS INHIBITORS OF MATRIX METALLOPROTEINASES

[75] Inventors: Bruce David Roth, Plymouth; Patrick Michael O'Brien, Stockbridge; Drago Robert Sliskovic, Saline, all of Mich.

[73] Assignee: Warner-Lambert Company, Ann Arbor, Mich.

[21] Appl. No.: 09/036,751

[22] Filed: Mar. 9, 1998

[51] Int. Cl.$^7$ .................................................. A01N 43/38

[52] U.S. Cl. .................. 514/411; 514/443; 514/468; 514/613; 514/675; 514/825; 514/885; 514/903; 548/440; 548/448; 548/449; 548/450; 548/512; 549/43; 549/44; 549/48; 549/460; 549/461; 564/189; 564/300; 568/306; 568/326

[58] Field of Search ................................. 549/461, 460, 549/43, 44, 48; 548/440, 448, 449, 450, 512; 564/189, 300; 568/306, 326; 514/825, 885, 903, 411, 443, 468, 613, 675

[56] References Cited

U.S. PATENT DOCUMENTS 4,239,765  12/1980  Regel et al. .............................. 548/262
5,627,206  5/1997  Hupe et al. .............................. 514/468

*Primary Examiner*—John Kight
*Assistant Examiner*—Raymond Covington
*Attorney, Agent, or Firm*—Merchant & Gould P.C.

[57] ABSTRACT

Fluorinated butyric acid compounds and derivatives are described as well as acid methods for the preparation and pharmaceutical compositions of same, which are useful as inhibitors of matrix metalloproteinases, particularly gelatinase A (72 kD gelatinase) and stromelysin-1, and also collagenase, matrilysin, and MMP-13, and for the treatment of multiple sclerosis, atherosclerotic plaque rupture, aortic aneurism, heart failure, restenosis, periodontal disease, corneal ulceration, treatment of burns, decubital ulcers, wound healing, cancer, inflammation, pain, arthritis, or other autoimmune or inflammatory disorders dependent upon tissue invasion by leukocytes or other activated migrating cells, acute and chronic neurodegenerative disorders including stroke, head trauma, spinal cord injury, Alzheimer's disease, amyotrophic lateral sclerosis, cerebral amyloid angiopathy, AIDS, Parkinson's disease, Huntington's disease, prion diseases, myasthenia gravis, and Duchenne's muscular dystrophy.

32 Claims, No Drawings

FLUORINATED BUTYRIC ACIDS AND THEIR DERIVATIVES AS INHIBITORS OF MATRIX METALLOPROTEINASES

BACKGROUND OF THE INVENTION

The present invention relates to novel fluorinated butyric acid compounds and their derivatives useful as pharmaceutical agents, to methods for their production, to pharmaceutical compositions which include these compounds and a pharmaceutically acceptable carrier, and to pharmaceutical methods of treatment. The novel compounds of the present invention are inhibitors of matrix metalloproteinases, e.g., gelatinase A (72 kDa gelatinase), stromelysin-1, collagenase, matrilysin, and matrix metalloproteinase-13 (MMP-13). More particularly, the novel compounds of the present invention are useful in the treatment of atherosclerotic plaque rupture, aortic aneurism, heart failure, restenosis, periodontal disease, corneal ulceration, treatment of burns, decubital ulcers, wound repair, cancer, inflammation, pain, arthritis, multiple sclerosis, and other autoimmune or inflammatory disorders dependent on the tissue invasion of leukocytes or other activated migrating cells. Additionally, the compounds of the present invention are useful in the treatment of acute and chronic neurodegenerative disorders including stroke, head trauma, spinal cord injury, Alzheimer's disease, amyotrophic lateral sclerosis, cerebral amyloid angiopathy, AIDS, Parkinson's disease, Huntington's disease, prion diseases, myasthenia gravis, and Duchenne's muscular dystrophy.

Gelatinase A and stromelysin-1 are members of the matrix metalloproteinase (MMP) family (Woessner J. F., *FASEB J.*, 1991;5:2145–2154). Other members include fibroblast collagenase, neutrophil collagenase, gelatinase B (92 kDa gelatinase), stromelysin-2, stromelysin-3, matrilysin, collagenase 3 (Freije J. M., Diez-Itza I., Balbin M., Sanchez L. M., Blasco R., Tolivia J., and Lopez-Otin C., *J. Biol. Chem.*, 1994;269:16766–16773), and the newly discovered membrane-associated matrix metalloproteinases (Sato H., Takino T., Okada Y., Cao J., Shinagawa A., Yamamoto E., and Seiki M., *Nature*, 1994;370:61–65).

The catalytic zinc in matrix metalloproteinases is a focal point for inhibitor design. The modification of substrates by introducing chelating groups has generated potent inhibitors such as peptide hydroxamates and thiol-containing peptides. Peptide hydroxamates and the natural endogenous inhibitors of MMPs (TIMPs) have been used successfully to treat animal models of cancer and inflammation.

The ability of the matrix metalloproteinases to degrade various components of connective tissue makes them potential targets for controlling pathological processes. For example, the rupture of an atherosclerotic plaque is the most common event initiating coronary thrombosis. Destabilization and degradation of the extracellular matrix surrounding these plaques by MMPs has been proposed as a cause of plaque fissuring. The shoulders and regions of foam cell accumulation in human atherosclerotic plaques show locally increased expression of gelatinase B, stromelysin-1, and interstitial collagenase. In situ zymography of this tissue revealed increased gelatinolytic and caseinolytic activity (Galis Z. S., Sukhova G. K., Lark M. W., and Libby P., "Increased expression of matrix metalloproteinases and matrix degrading activity in vulnerable regions of human atherosclerotic plaques", *J. Clin. Invest.*, 1994;94:2494–2503). In addition, high levels of stromelysin RNA message have been found to be localized to individual cells in atherosclerotic plaques removed from heart transplant patients at the time of surgery (Henney A. M., Wakeley P. R., Davies M. J., Foster K., Hembry R., Murphy G., and Humphries S., "Localization of stromelysin gene expression in atherosclerotic plaques by in situ hybridization", *Proc. Nat'l. Acad. Sci.*, 1991;88:8154–8158).

Inhibitors of matrix metalloproteinases will have utility in treating degenerative aortic disease associated with thinning of the medial aortic wall. Increased levels of the proteolytic activities of MMPs have been identified in patients with aortic aneurisms and aortic stenosis (Vine N. and Powell J. T., "Metalloproteinases in degenerative aortic diseases", *Clin. Sci.*, 1991;81:233–239).

Heart failure arises from a variety of diverse etiologies, but a common characteristic is cardiac dilation, which has been identified as an independent risk factor for mortality (Lee T. H., Hamilton M. A., Stevenson L. W., Moriguchi J. D., Fonarow G. C., Child J. S., Laks H., and Walden J. A., "Impact of left ventricular size on the survival in advanced heart failure", *Am. J. Cardiol.*, 1993;72:672–676). This remodeling of the failing heart appears to involve the breakdown of extracellular matrix. Matrix metalloproteinases are increased in patients with both idiopathic and ischemic heart failure (Reddy H. K., Tyagi S. C., Tjaha I. E., Voelker D. J., Campbell S. E., and Weber K. T., "Activated myocardial collagenase in idiopathic dilated cardiomyopathy", *Clin. Res.*, 1993;41:660A; Tyagi S.C., Reddy H. K., Voelker D., Tjara I. E., and Weber K. T., "Myocardial collagenase in failing human heart", *Clin. Res.*, 1993;41:681A). Animal models of heart failure have shown that the induction of gelatinase is important in cardiac dilation (Armstrong P. W., Moe G. W., Howard R. J., Grima E. A., and Cruz T. F., "Structural remodeling in heart failure: gelatinase induction", *Can. J. Cardiol.*, 1994;10:214–220), and cardiac dilation precedes profound deficits in cardiac function (Sabbah H. N., Kono T., Stein P. D., Mancini G. B., and Goldstein S., "Left ventricular shape changes during the course of evolving heart failure", *Am. J. Physiol.*, 1992;263:H266–270).

Neointimal proliferation, leading to restenosis, frequently develops after coronary angioplasty. The migration of vascular smooth muscle cells (VSMCs) from the tunica media to the neointima is a key event in the development and progression of many vascular diseases and a highly predictable consequence of mechanical injury to the blood vessel (Bendeck M. P., Zempo N., Clowes A. W., Galardy R. E., and Reidy M., "Smooth muscle cell migration and matrix metalloproteinase expression after arterial injury in the rat", *Circulation Research*, 1994;75:539–545). Northern blotting and zymographic analyses indicated that gelatinase A was the principal MMP expressed and excreted by these cells. Further, antisera capable of selectively neutralizing gelatinase A activity also inhibited VSMC migration across basement membrane barrier. After injury to the vessel, gelatinase A activity increased more than 20-fold as VSMCs underwent the transition from a quiescent state to a proliferating, motile phenotype (Pauly R. R., Passaniti A., Bilato C., Monticone R., Cheng L., Papadopoulos N., Gluzband Y. A., Smith L., Weinstein C., Lakatta E., and Crow M. T., "Migration of cultured vascular smooth muscle cells through a basement membrane barrier requires type IV collagenase activity and is inhibited by cellular differentiation", *Circulation Research*, 1994;75:41–54).

Collagenase and stromelysin activities have been demonstrated in fibroblasts isolated from inflamed gingiva (Uitto V. J., Applegren R., and Robinson P. J., "Collagenase and neutral metalloproteinase activity in extracts from inflamed human gingiva", *J. Periodontal Res.*, 1981;16:417–424), and enzyme levels have been correlated to the severity of gum disease (Overall C. M., Wiebkin O. W., and Thonard J. C., "Demonstrations of tissue collagenase activity in vivo and its relationship to inflammation severity in human gingiva", *J. Periodontal Res.*, 1987;22:81–88). Proteolytic degradation of extracellular matrix has been observed in corneal ulceration following alkali burns (Brown S. I., Weller C. A., and Wasserman H. E., "Collagenolytic activity of alkali burned corneas", *Arch. Ophthalmol.*, 1969;81:370–373). Thiol-containing peptides inhibit the collagenase isolated from alkali-burned rabbit corneas (Burns F. R., Stack M. S., Gray R. D., and Paterson C. A., *Invest. Ophthalmol.*, 1989;30:1569–1575).

Stromelysin is produced by basal keratinocytes in a variety of chronic ulcers (Saarialho-Kere U. K., Ulpu K., Pentland A. P., Birkedal-Hansen H., Parks W. O., and Welgus H. G., "Distinct Populations of Basal Keratinocytes Express Stromelysin-1 and Stromelysin-2 in Chronic Wounds", *J. Clin. Invest.*, 1994;94:79–88).

Stromelysin-1 mRNA and protein were detected in basal keratinocytes adjacent to but distal from the wound edge in what probably represents the sites of the proliferating epidermis. Stromelysin-1 may thus prevent the epidermis from healing.

Davies, et al., (*Cancer Res.*, 1993;53:2087–2091) reported that a peptide hydroxymate, BB-94, decreased the tumor burden and prolonged the survival of mice bearing human ovarian carcinoma xenografts. A peptide of the conserved MMP propeptide sequence was a weak inhibitor of gelatinase A and inhibited human tumor cell invasion through a layer of reconstituted basement membrane (Melchiori A., Albili A., Ray J. M., and Stetler-Stevenson W. G., *Cancer Res.*, 1992;52:2353–2356). The natural tissue inhibitor of metalloproteinase-2 (TIMP-2) also showed blockage of tumor cell invasion in in vitro models (DeClerck Y. A., Perez N., Shimada H., Boone T. C., Langley K. E., and Taylor S. M., *Cancer Res.*, 1992;52:701–708). Studies of human cancers have shown that gelatinase A is activated on the invasive tumor cell surface (Strongin A. Y., Marmer B. L., Grant G. A., and Goldberg G. I., *J. Biol. Chem.*, 1993;268:14033–14039) and is retained there through interaction with a receptor-like molecule (Monsky W. L., Kelly T., Lin C. -Y., Yeh Y., Stetler-Stevenson W. G., Mueller S. C., and Chen W. -T., *Cancer Res.*, 1993;53:3159–3164).

Inhibitors of MMPs have shown activity in models of tumor angiogenesis (Taraboletti G., Garofalo A., Belotti D., Drudis T., Borsotti P., Scanziani E., Brown P. D., and Giavazzi R., *Journal of the National Cancer Institute*, 1995;87:293 and Benelli R., Adatia R., Ensoli B., Stetler-Stevenson W. G., Santi L., and Albini A, *Oncolocy Research*, 1994;6:251–257).

Several investigators have demonstrated consistent elevation of stromelysin and collagenase in synovial fluids from rheumatoid and osteoarthritis patients as compared to controls (Walakovits L. A., Moore V. L., Bhardwaj N., Gallick G. S., and Lark M. W., "Detection of stromelysin and collagenase in synovial fluid from patients with rheumatoid arthritis and post-traumatic knee injury", *Arthritis Rheum.*, 1992;35:35–42; Zafarullah M., Pelletier J. P., Cloutier J. M., and Marcel-Pelletier J., "Elevated metalloproteinases and tissue inhibitor of metalloproteinase mRNA in human osteoarthritic synovia", *J. Rheumatol.*, 1993;20:693–697). TIMP-1 and TIMP-2 prevented the formation of collagen fragments, but not proteoglycan fragments in both the bovine nasal and pig articular cartilage models for arthritis, while a synthetic peptide hydroxamate could prevent the formation of both fragments (Andrews H. J., Plumpton T. A., Harper G. P., and Cawston T. E., *Agents Actions*, 1992;37:147–154; Ellis A. J., Curry V. A., Powell E. K., and Cawston T. E., *Biochem. Biophys. Res. Commun.*, 1994;201:94–101).

Gijbels, et al., (*J. Clin. Invest.*, 1994;94:2177–2182) recently described a peptide hydroxamate, GM6001, that suppressed the development or reversed the clinical expression of experimental autoimmune encephalomyelitis (EAE) in a dose dependent manner, suggesting the use of MMP inhibitors in the treatment of autoimmune inflammatory disorders such as multiple sclerosis.

A recent study by Madri has elucidated the role of gelatinase A in the extravasation of T-cells from the blood stream during inflammation (Ramanic A. M., and Madri J. A., "The Induction of 72-kDa Gelatinase in T Cells upon Adhesion to Endothelial Cells is VCAM-1 Dependent", *J. Cell Biology*, 1994;125:1165–1178). This transmigration past the endothelial cell layer is coordinated with the induction of gelatinase A and is mediated by binding to the vascular cell adhesion molecule-1 (VCAM-1). Once the barrier is compromised, edema and inflammation are produced in the CNS. Also, leukocytic migration across the blood-brain barrier is known to be associated with the inflammatory response in EAE. Inhibition of the metalloproteinase gelatinase A would block the degradation of extracellular matrix by activated T-cells that is necessary for CNS penetration.

These studies provide the basis for the expectation that an effective inhibitor of gelatinase A and/or stromelysin-1 would have value in the treatment of diseases involving disruption of extracellular matrix resulting in inflammation due to lymphocytic infiltration, inappropriate migration of metastatic or activated cells, or loss of structural integrity necessary for organ function.

Neuroinflammatory mechanisms are implicated in a broad range of acute and chronic neurodegenerative disorders, including stroke, head trauma, multiple sclerosis, and Alzheimer's disease, to name a few (McGeer E. G. and McGeer P. L., "Neurodegeneration and the immune system", In: Calne D. B., ed. Neurodegenerative Diseases, W. B. Saunders, 1994:277–300). Other disorders that may involve neuroinflammatory mechanisms include amyotrophic lateral sclerosis (Leigh P. N., "Pathogenic mechanisms in amyotrophic lateral sclerosis and other motor neuron disorders", In: Calne D. B., ed., Neurodegenerative Diseases, W. B. Saunders, 1994:473–88), cerebral amyloid angiopathy (Mandybur T. I. and Balko G., "Cerebral amyloid angiopathy with granulomatous angiitis ameliorated by steroid-cytoxan treatment", *Clin. Neuropharm.*, 1992;15:241–7), AIDS (Gendelman H. E. and Tardieu M., "Macrophages/microglia and the pathophysiology of CNS injuries in AIDS", *J. Leukocyte Biol.*, 1994;56:387–8), Parkinson's disease, Huntington's disease, prion diseases, and certain disorders involving the peripheral nervous system, such as myasthenia gravis and Duchenne's muscular dystrophy. Neuroinflammation, which occurs in response to brain injury or autoimmune disorders, has been shown to cause destruction of healthy tissue (Martin R., MacFarland H. F., and McFarlin D. E., "Immunological aspects of demyelinating diseases", *Annul Rev. Immunol.*, 1992;10:153–87; Clark R. K., Lee E. V., Fish C. J., et al., "Development of tissue damage, inflammation and resolution following stroke: an immunohistochemical and quantitative planimetric study", *Brain Res. Bull.*, 1993;31:565–72; Giulian D. and Vaca K., "Inflammatory glia mediate delayed neuronal damage after ischemia in the central nervous system", *Stroke*, 1993;24(Suppl 12):184–90; Patterson P. H., "Cytokines in Alzheimer's disease and multiple sclerosis", *Cur. Opinion Neurobiol.*, 1995;5:642–6; McGeer P. L., Rogers J., and McGeer E. G., "Neuroimmune mechanisms in Alzheimer disease pathogenesis", *Alzheimer Dis. Assoc. Disorders,* 1994;8:149–58; Martin R. and McFarland H. F., "Immunological aspects of experimental allergic encephalomyelitis and multiple sclerosis", *Crit. Rev. Clin. Lab. Sci.,* 1995;32:121–82; Rogers J., Webster S., Lue L. F., et al., "Inflammation and Alzheimer's disease pathogenesis", In: *Neurobiology of Aging*, in press; Rothwell N. J. and Relton J. K., "Involvement of cytokines in acute neurodegeneration in the CNS", *Neurosci. Biobehav. Rev.,* 1993;17:217–27). The pathological profiles and clinical courses of these disorders differ widely, but they all have in common the participation of immune/inflammatory elements in the disease process. In particular, many neurodegenerative disorders are characterized by large numbers of reactive microglia in postmortem brain samples, indicative of an active inflammatory process (McGeer E. G. and McGeer P. L., supra., 1994).

Increasing attention is being directed toward inflammatory mechanisms in Alzheimer's disease. Several lines of evidence support the involvement of neuroinflammation in Alzheimer's disease: 1) There is a significant increase in inflammatory markers in the Alzheimer brain, including acute phase reactants, cytokines, complement proteins, and MHC molecules (McGeer et al., supra., 1994; Rogers et al., supra., in press); 2) There is evidence that β-amyloid induces neurodegenerative changes primarily through interactions with inflammatory molecules, and that inflammation alone is sufficient to induce neurodegeneration (Rogers et al., supra., in press); and 3) Growing epidemiological data indicate that antiinflammatory therapy can delay the onset and slow the progression of Alzheimer's disease (McGeer P. L. and Rogers J., "Anti-inflammatory agents as a therapeutic approach to Alzheimer's disease", *Neurology*, 1992;42:447–9; Canadian Study of Health and Aging, "Risk factors for Alzheimer's disease in Canada", *Neurology,* 1994;44:2073–80; Lucca U., Tettamanti M., Forloni G., and Spagnoli A., "Nonsteroidal antiinflammatory drug use in Alzheimer's disease", *Biol. Psychiatry,* 1994;36:854–66; Hampel H. and Müller N., "Inflammatory and immunological mechanisms in Alzheimer's disease", *DN&P,* 1995;8:599–608; Breitner J. C. S., Gau B. A., Welsh K. A., et al., "Inverse association of anti-inflammatory treatments and Alzheimer's disease: Initial results of a co-twin control study", *Neurology,* 1994;44:227–32; Breitner J. C. S., Welsh K. A., Helms M. J., et al., "Delayed onset of Alzheimer's disease with nonsteroidal anti-inflammatory and histamine H2 blocking drugs", *Neurobiol. Aging,* 1995;16:523–30; Andersen K., Launer L. J., Ott A., Hoes A. W., Breteler M. M. B., and Hofman A., "Do nonsteroidal anti-inflammatory drugs decrease the risk for Alzheimer's disease? The Rotterdam Study", *Neurology,* 1995;45:1441–5; Rich J. B., Rasmusson D. X., Folstein M. F., et al., "Nonsteroidal anti-inflammatory drugs in Alzheimer's disease", *Neurology,* 1995;45:51–5; Aisen P. S., "Anti-inflammatory therapy for Alzheimer's disease", *Dementia,* 1995;9:173–82; Rogers, et al., supra., in press). Chronic use of nonsteroidal antiinflammatory drugs (NSAIDs), most commonly for the treatment of rheumatoid arthritis, decreases the probability of developing Alzheimer's disease, and there is reason to believe that other antiinflammatory agents may also be effective, although direct evidence for the efficacy of such treatments is lacking (Hamper and M üller, supra., 1995). Furthermore, virtually all of the currently available compounds, which include corticosteroids, NSAIDs, antimalarial drugs, and colchicine, have serious drawbacks that make them undesirable in the treatment of chronic disorders. Glucocorticoids, which are in wide clinical use as antiinflammatory/immuno-suppressive drugs, can be directly neurotoxic and also are toxic to systemic organs at moderate to high doses. NSAIDs have gastrointestinal and renal side effects that obviate long-term use in most people, and few of them cross the blood-brain barrier in significant amounts. The toxic properties of chloroquine compounds and colchicine also are well known. An antiinflammatory drug that is well-tolerated by patients and that crosses the blood-brain barrier has significant advantages for the treatment of acute and chronic degenerative diseases of the central nervous system.

We have identified a series of fluorinated butyric acid compounds and derivatives that are inhibitors of matrix metalloproteinases, particularly stromelysin-1 and gelatinase A, and also collagenase, matrilysin, and MMP-13, and thus are useful as agents for the treatment of multiple sclerosis, atherosclerotic plaque rupture, restenosis, aortic aneurism, heart failure, periodontal disease, corneal ulceration, treatment of burns, decubital ulcers, wound repair, cancer, inflammation, pain, arthritis, or other autoimmune or inflammatory diseases dependent upon tissue invasion by leukocytes or other activated migrating cells, acute and chronic neurodegenerative disorders including stroke, head trauma, spinal cord injury, Alzheimer's disease, amyotrophic lateral sclerosis, cerebral amyloid angiopathy, AIDS, Parkinson's disease, Huntington's diseases, prion diseases, myasthenic gravis, and Duchenne's muscular dystrophy.

SUMMARY OF THE INVENTION

Accordingly, the present invention is a compound of Formula I

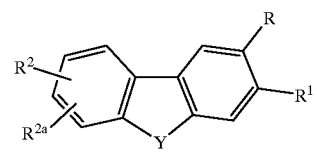

wherein one of R or $R^1$ is hydrogen and the other is

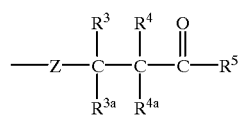

wherein

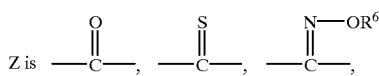

wherein
$R^6$ is hydrogen,
alkyl,
—$(CH_2)_n$-aryl wherein n is zero or an integer of 1 to 5, or —(CH$_2$)$_n$-cycloalkyl wherein n is as defined above, or

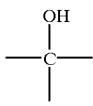

R$^3$, R$^{3a}$, R$^4$, and R$^{4a}$ are independently the same or different and are hydrogen,
fluorine,
alkyl,
—(CH$_2$)$_n$-aryl wherein n is as defined above,
—(CH$_2$)$_n$—N-phthalimido wherein n is as defined above, or
—(CH$_2$)$_n$-heteroaryl wherein n is as defined above, and
R$^5$ is OH or
NH—OH, or

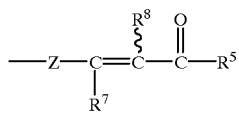

wherein
R$^7$ and R$^8$ are independently the same or different and are hydrogen or fluorine and Z and R$^5$ are as defined above;
R$^2$ is hydrogen,
alkyl,
alkoxy,
halogen,
hydroxy,
cyano,
nitro,
trifluoromethyl,

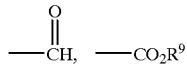

wherein
R$^9$ is hydrogen or
alkyl,
—COR$^9$ wherein R$^9$ is as defined above,
—SO$_3$R$^9$ wherein R$^9$ is as defined above,

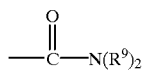

wherein
R$^9$ is as defined above, or
(CH$_2$)$_n$N(R$^9$)$_2$ wherein n and R$^9$ are as defined above;
R$^{2a}$ is hydrogen,
alkyl,
alkoxy,
halogen,
hydroxy, or
cyano; and
Y is

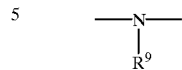

wherein
R$^9$ is as defined above,
—O—,
—S(O)$_m$— wherein m is zero or an integer of 1 or 2,

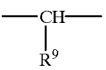

wherein
R$^9$ is as defined above,

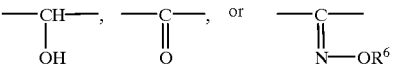

wherein
R$^6$ is as defined above;
with the proviso that at least one of R$^3$, R$^{3a}$, R$^4$, or R$^{4a}$ is fluorine and at least one of R$^7$ and R$^8$ is fluorine;
and corresponding isomers thereof; a pharmaceutically acceptable prodrug thereof; or a pharmaceutically acceptable salt thereof.

As matrix metalloproteinase inhibitors, the compounds of Formula I are useful as agents for the treatment of multiple sclerosis. They are also useful as agents for the treatment of atherosclerotic plaque rupture, aortic aneurism, heart failure, restenosis, periodontal disease, corneal ulceration, treatment of burns, decubital ulcers, wound repair, cancer metastasis, tumor angiogenesis, inflammation, pain, arthritis, and other autoimmune or inflammatory disorders dependent upon tissue invasion by leukocytes or other activated migrating cells, acute and chronic neurodegenerative disorders including stroke, head trauma, spinal cord injury, Alzheimer's disease, amyotrophic lateral sclerosis, cerebral amyloid angiopathy, AIDS, Parkinson's disease, Huntington's disease, prion diseases, myasthenia gravis, and Duchenne's muscular dystrophy.

A still further embodiment of the present invention is a pharmaceutical composition for administering an effective amount of a compound of Formula I in unit dosage form in the treatment methods mentioned above. Finally, the present invention is directed to methods for production of compounds of Formula I.

DETAILED DESCRIPTION OF THE INVENTION

In the compounds of Formula I, the term "alkyl" means a straight or branched hydrocarbon radical having from 1 to 8 carbon atoms and includes, for example, methyl, ethyl, n-propyl, isopropyl, n-butyl, sec-butyl, isobutyl, tert-butyl, n-pentyl, n-hexyl, n-heptyl, n-octyl, and the like.

"Alkoxy" and "thioalkoxy" are O-alkyl or S-alkyl of from 1 to 6 carbon atoms as defined above for "alkyl".

The term "cycloalkyl" means a saturated hydrocarbon ring having 3 to 8 carbon atoms and includes, for example, cyclopropyl, cyclobutyl, cyclopentyl, cyclohexyl, cycloheptyl, cyclooctyl, and the like.

The term "aryl" means an aromatic radical which is a phenyl group, a naphthyl group or a phenyl group or a naphthyl group substituted by 1 to 4 substituents selected from alkyl as defined above, alkoxy as defined above, thioalkoxy as defined above, hydroxy, halogen, trifluoromethyl, amino, alkylamino as defined above for alkyl, dialkylamino as defined above for alkyl, nitro, cyano, carboxy, SO$_3$H, CHO,

as defined above for alkyl,

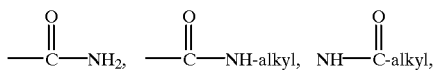

as defined above for alkyl,

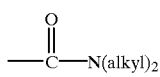

as defined above for alkyl, —(CH$_2$)$_n$—NH$_2$ wherein n is an integer of 1 to 5, —(CH$_2$)$_n$—NH-alkyl as defined above for alkyl and n, —(CH$_2$)$_n$—N(alkyl)$_2$ as defined above for alkyl and n,

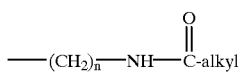

as defined above for alkyl, and n and

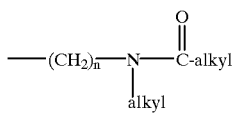

as defined above for alkyl and n.

The term "heteroaryl" means a heteroaromatic radical and includes, for example, a heteroaromatic radical which is 2- or 3-thienyl, 2- or 3-furanyl, 2- or 3-pyrrolyl, 2-, 3-, or 4-pyridinyl, 2-pyrazinyl, 2-, 4-, or 5-pyrimidinyl, 3- or 4-pyridazinyl, 1H-indol-6-yl, 1H-indol-5-yl, 1H-benzimidazol-6-yl, 1H-benzimidazol-5-yl, 2-, 4-, or 5-thiazolyl, 3-, 4-, or 5-isothiazolyl, 2-, 4-, or 5-imidazolyl, 3-, 4-, or 5-pyrazolyl, or 2- or 5-thiadiazolyl.

"Halogen" is fluorine, chlorine, bromine, or iodine.

"Host" means mammals, including humans.

The term "pharmaceutically acceptable prodrug" means a compound of Formula I which is biotransformed in a mammal to a pharmacologically active compound. Thus, for example, in the case of an ester prodrug of a compound of Formula I wherein R$^5$ is OR$^{10}$, wherein R$^{10}$ is alkyl or benzyl the ester prodrug is biotransformed to the pharmacologically active acid wherein R$^5$ is OH.

Some of the compounds of Formula I are capable of further forming both pharmaceutically acceptable acid addition and/or base salts. All of these forms are within the scope of the present invention.

Pharmaceutically acceptable acid addition salts of the compounds of Formula I include salts derived from nontoxic inorganic acids such as hydrochloric, nitric, phosphoric, sulfuric, hydrobromic, hydriodic, hydrofluoric, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge S. M., et al., "Pharmaceutical Salts," *J. of Pharma. Sci.*, 1977;66:1).

The acid addition salts of said basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge S. M., et al., "Pharmaceutical Salts," *J. of Pharma Sci.*, 1977;66:1).

The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

Certain of the compounds of the present invention possess one or more chiral centers and each center may exist in the R or S configuration. The present invention includes all diastereomeric, enantiomeric, and epimeric forms as well as the appropriate mixtures thereof. Additionally, the compounds of the present invention may exist as geometric isomers. The present invention includes all cis, trans, syn, anti, entgegen (E), and zusammen (Z) isomers as well as the appropriate mixtures thereof.

A preferred compound of Formula I is one wherein R is

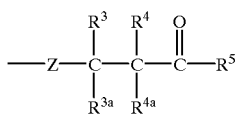

wherein Z is

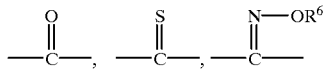

wherein
R⁶ is hydrogen,
alkyl,
—(CH₂)$_n$-aryl wherein n is zero or an integer of 1 to 5, or
(CH₂)$_n$-cycloalkyl wherein n is as defined above, or

R³, R³$^a$, R⁴, and R⁴$^a$ are independently the same or different and are hydrogen,
fluorine,
alkyl,
—(CH₂)$_n$-aryl wherein n is as defined above,
—(CH₂)$_n$—N-phthalimido wherein n is as defined above, or
—(CH₂)$_n$-heteroaryl wherein n is as defined above, and
R⁵ is OH or
NH—OH, or

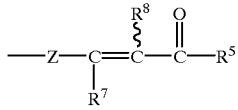

wherein
R⁷ and R⁸ are independently the same or different and are hydrogen or fluorine and Z and R⁵ are as defined above;
R¹ is hydrogen; and
Y is —O—, or
—CH₂—.

Another preferred compound of Formula I is one wherein R¹, R², and R²$^a$ are hydrogen.
Another preferred compound of Formula I is one wherein R is

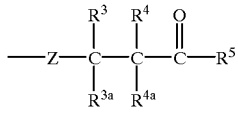

wherein
Z is

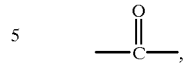

R³ and R³$^a$ are hydrogen or fluorine,
R⁴ and R⁴$^a$ are hydrogen,
—(CH₂)$_n$-aryl wherein n is zero or an integer of 1 to 5,
—(CH₂)$_n$—N-phthalimido wherein n is as defined above, or
—(CH₂)$_n$-heteroaryl wherein n is as defined above, and
R⁵ is OH or
NH—OH.

A more preferred compound of Formula I is one wherein R⁵ is OH.

A most preferred compound of Formula I is one wherein Z is

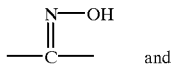 and

R⁵ is OH.

Particularly valuable is a compound selected from the group consisting of:
2-Benzyl-4-dibenzofuran-2-yl-3,3-difluoro-4-oxo-butyric acid;
4-Dibenzofuran-2-yl-3,3-difluoro-4-hydroxyimino-butyric acid;
4-Dibenzofuran-2-yl-3,3-difluoro-N-hydroxy-4-oxo-butyramide;
4-Dibenzofuran-2-yl-3-fluoro-4-oxo-but-2-enoic acid;
4-Dibenzofuran-2-yl-3,3-difluoro-4-thioxo-butyric acid;
4-Dibenzofuran-2-yl-3,3-difluoro-4-hydroxy-butyric acid;
4-(7-Bromo-dibenzofuran-2-yl)-3,3-difluoro-4-oxo-butyric acid;
3,3-Difluoro-4-(8-hydroxy-dibenzofuran-2-yl)-4-oxo-butyric acid;
4-Dibenzofuran-2-yl-3,3-difluoro-4-oxo-butyric acid;
4-Dibenzofuran-2-yl-2,3-difluoro-4-oxo-2-phenethyl-butyric acid;
4-Dibenzofuran-2-yl-2,2-difluoro-4-hydroxyimino-butyric acid;
3-(Dibenzofuran-2-carbonyl)-2-fluoro-5-pyridin-2-yl-pentanoic acid;
2-(2-Dibenzofuran-2-yl-1,1-difluoro-2-oxo-ethyl)-5-(1,3-dioxo-1,3-dihydro-isoindol-2-yl)-pentanoic acid;
3-Fluoro-4-methoxyimino-4-(7-nitro-dibenzofuran-2-yl)-butyric acid;
4-(9H-Fluoren-2-yl)-3,3-difluoro-4-oxo-butyric acid;
4-(7-Bromo-9H-fluoren-3-yl)-2,2-difluoro-4-hydroxyimino-butyric acid;
4-(9H-Fluoren-2-yl)-2,3-difluoro-N-hydroxy-4-oxo-butyramide;
4-Dibenzothiophen-2-yl-2,2,3,3-tetrafluoro-4-oxo-butyric acid;
2-Benzyl-4-dibenzothiophen-2-yl-3-fluoro-4-oxo-butyric acid;
4-Dibenzothiophen-2-yl-2,3-difluoro-4-oxo-but-2-enoic acid;

4-(9H-Carbazol-2-yl)-2,2-difluoro-4-hydroxyimino-butyric acid;

3-Fluoro-4-(9-methyl-9H-carbazol-2-yl)-4-oxo-butyric acid;

4-Dibenzofuran-2-yl-2,2-difluoro-4-oxo-butyric acid;

4-(7-Bromo-9H-fluoren-3-yl)-2,2-difluoro-4-oxo-butyric acid;

4-Dibenzofuran-2-yl-2,3-difluoro-4-oxo-butyric acid;

4-Dibenzofuran-2-yl-2-fluoro-4-oxo-butyric acid;

3-Fluoro-4-(7-nitrodibenzofuran-2-yl)-butyric acid;

4-Dibenzothiophen-2-yl-3-fluoro-4-oxo-butyric acid; and 4-(9H-Fluoren-3-yl)-2,2-difluoro-4-hydroxyimino-butyric acid;

and corresponding isomers thereof; a pharmaceutically acceptable prodrug thereof; or a pharmaceutically acceptable salt thereof.

A particularly valuable compound of Formula I is 4-dibenzofuran-2-yl-2,2-difluoro-4-oxo-butyric acid; a pharmaceutically acceptable prodrug thereof; or a pharmaceutically acceptable salt thereof.

A most particularly valuable compound of Formula I is 4-dibenzofuran-2-yl-3,3-difluoro-4-oxo-butyric acid; a pharmaceutically acceptable prodrug thereof; or a pharmaceutically acceptable salt thereof.

The compounds of Formula I are valuable inhibitors of gelatinase A and/or stromelysin-1. Additionally, the compounds of Formula I are inhibitors of collagenase, matrilysin, and MMP-13. It has been shown previously that inhibitors of matrix metalloproteinases have efficacy in models of disease states like arthritis and metastasis that depend on modification of the extracellular matrix.

In vitro experiments were carried out which demonstrate the efficacy of compounds of Formula I as potent and specific inhibitors of gelatinase A and stromelysin-1. Experiments were carried out with the catalytic domains of the proteinases. Table 1 shows the activity of Examples 1–2 versus GCD (recombinant gelatinase A catalytic domain) and SCD (stromelysin-1 catalytic domain). $IC_{50}$ values were determined using a thiopeptolide substrate, Ac-Pro-Leu-Gly-thioester-Leu-Leu-Gly-OEt (Ye Q. -Z., Johnson L. L., Hupe D. J., and Baragi V., "Purification and Characterization of the Human Stromelysin Catalytic Domain Expressed in *Escherichia coli*", *Biochemistry*, 1992;31:11231–11235).

TABLE 1

| Example | $IC_{50}$ ($\mu$M) | |
| --- | --- | --- |
| | GCD | SCD |
| 1 | 1.95 | 24 |
| 2 | 93.6 | >100 |

Compounds of Formula I can be prepared according to the procedures outlined in Schemes 1–6 and unless otherwise indicated $R^2$, $R^{2a}$, $R^3$, $R^{3a}$, $R^4$, $R^{4a}$, $R^6$, $R^7$, $R^8$, and Y are as defined previously. Appropriately substituted succinic anhydrides (2–5), which are known in the art, undergo Friedel-Craft acylation reactions with the unsubstituted aryl ring of a compound of Formula II in the presence of aluminum chloride ($AlCl_3$) in a solvent such as, for example, dichloromethane ($CH_2Cl_2$), dichloroethane ($C_2H_4Cl_2$), and the like at temperatures ranging from about 0° to about 85° C. to give the corresponding fluorinated butyric acid derivatives (6–10). Unsymmetrical anhydrides, such as Compounds 2 and 3 in Scheme 1, yield a mixture of regioisomers (6,7 and 8,9 respectively) that can be separated utilizing silica gel chromatography. Similarly, using Friedel-Craft reaction conditions, Compounds 10 and 11 can be prepared from symmetrical fluorinated anhydrides 4 and 5. The regiochemistry of the aryl ring using these reaction conditions is dependent on the Y substituent. For example, dibenzofuran (Y=O) and dibenzothiophene (Y=S) afford 2-isomeric products, i.e., para to the Y substituent using Friedel-Craft reaction conditions, whereas fluorene (Y=CH) and carbazole (Y=NH) yield the 3-isomeric products, i.e., meta to the Y substituent.

The ketone moiety of the fluorinated derivatives 6–11 can be reduced to the corresponding alcohols (12–17) using sodium borohydride ($NaBH_4$) in a solvent such as, for example, ethanol (EtOH), tetrahydrofuran (THF) and the like at 25° C. to 80° C. or converted to thioketones (24–29) when allowed to react with Lawesson's reagent (2,4-bis(4-methoxyphenyl)-1,3-dithia-2,4-diphosphetane-2,4-disulfide) in a solvent such as, for example, tetrahydrofuran and the like at a temperature range between about 0° C. and about reflux. Alternatively, oximes 36–41 can be prepared from compounds 6–11 when reacted with appropriately substituted hydroxylamines in a solution of pyridine in ethanol at a temperature range between about 25° and about 85° C. The carboxylic acid functionalities of the fluorinated derivatives (6–11, 12–17, 24–29, 36–41) can be coupled with appropriately substituted hydroxylamines in the presence of a suitable coupling agent, such as, for example, carbonyldiimidazole (CDI), dicyclohexylcarbodiimide (DCC), and the like in a solvent such as, for example, in tetrahydrofuran and the like at about 0° C. to about 65° C., to give the corresponding hydroxamate or hydroxamic acid derivatives (18–23, 30–35, 42–47, 48–53) shown in Scheme 1.

Alternatively, Compounds 6–11 can be prepared from 2- or 3-bromine-substituted tricyclic ring systems of Formula 54 (Scheme 2). Halogen-metal exchange occurs with n-butyllithium (n-BuLi) in tetrahydrofuran at a temperature as low as −78° C., followed by treatment of the lithiated derivative with tri-n-butyltin chloride ($ClSnBu_3$) to give the corresponding tin reagent (55). This reactive intermediate can be converted to a keto-ester of Formula 57 via bis (triphenylphosphine)-palladium (II) chloride ($Cl_2Pd(Ph_3P)_2$) catalyzed coupling of appropriately substituted acid chlorides (56) with 55 in a solvent such as, for example, tetrahydrofuran, p-dioxane and the like at temperatures between about −20° C. and about reflux. Hydrolysis of the ester (57) to the corresponding keto-acids (6–11) is best carried out using sodium hydroxide (NaOH) in ethanol.

As shown in Scheme 3, Friedel-Craft reaction conditions were also used to incorporate unsaturation into the keto-acid sidechain. Fluorinated maleic anhydride derivatives (58,59), which are known in the art, are coupled with a compound of Formula II in a solvent such as, for example, dichloromethane and the like in the presence of aluminum chloride at about 0° C. As in Scheme 1, the unsymmetrical anhydride (58) yields an isomeric mixture (60,61), which can be separated using silica gel chromatography, whereas acylation of 59 affords only Compound 62. Isomeric mixtures (i.e., cis/trans) that may result using these reaction conditions can also be separated using silica gel chromatography. For Compounds 60–62, the ketone and carboxylic acid moieties can be converted to functionalities previously described in Scheme 1.

The fluorinated side chain of compounds of this invention can be further functionalized as shown in Scheme 4. The alcohol of commercially available dimethyl malate (63) is protected using tert-butyldimethylsilyl chloride (TBDMSCl) and imidazole in a solvent such as, for example, dimethylformamide and the like at about 25° C. The protected malate derivative (64) can be taken up in tetrahydrofuran, cooled between about −20° C. and about −78° C., and treated with lithium diisopropylamide (LDA). To this cold solution is added an appropriately substituted alkyl halide (Br(CH$_2$)$_n$A) wherein A is aryl, heteroaryl, or phthalimido which on warming to a temperature between about 25° C. and about reflux, gives Compound 65. Hydrolysis of 65 to the half ester using one equivalent of potassium hydroxide (KOH) in ethanol affords a mixture of Compounds 66 and 67. This mixture can be converted to the corresponding acid chloride derivatives (68,69) upon treatment with oxalyl chloride in dichloromethane and a catalytic amount of dimethylformamide. Utilizing the Friedel-Craft conditions previously described in Scheme 1, followed by deprotection of the alcohol with tetrabutylammonium fluoride (nBu$_4$NF) in aqueous tetrahydrofuran at about 25° C., affords a mixture of Compounds 70 and 71, each of which can be isolated using silica gel chromatography. Alcohols 70 and 71 are fluorinated using diethylaminosulfurtrifluoride (DAST) in a solvent such as, for example, dichloromethane, chloroform and the like at temperatures between about −20° C. and about reflux with subsequent hydrolysis of the esters using sodium hydroxide (NaOH) in ethanol at about room temperature to give the mono-fluorinated derivatives 72 and 73.

The alpha and beta bis-fluorine derivatives, Compounds 6 and 7, can also be coupled with appropriately substituted alkyl halides as shown in Scheme 5. Deprotonation of the methylene alpha to either the acid, as in 6, or the ketone in 7, occurs upon treatment with 2 equivalents of lithium diisopropylamide (LDA) in a solvent such as, for example, tetrahydrofuran and the like at a temperature between about −20° C. and about −78° C. Addition of an appropriately substituted alkyl halide (Br(CH$_2$)$_n$A) wherein A is aryl, heteroaryl, or phthalimido followed by warming the reaction mixture between about 25° C. and about reflux, yields the corresponding alkylated derivatives (74,75).

Scheme 6 provides additional synthetic routes capable of incorporating the —(CH$_2$)$_n$A group wherein A is aryl, heteroaryl, or phthalimido in the fluorinated side chain of analogs of Formula I in either the alpha or beta position relative to the acid moiety. The first synthetic route involves Friedel-Craft acylation of a compound of Formula II with bromoacetyl chloride to give intermediate 76 using reaction conditions previously described. The ester (77), derived from commercially available fluoroacetic acid, methyl ester, is treated with one equivalent of LDA in a solvent such as, for example, tetrahydrofuran and the like at about −78° C. and coupled with the bromoacetophenone derivative (76) to give the keto-ester 78. This product is taken up in tetrahydrofuran and cooled between about −20° C. and about −78° C. before adding one equivalent of lithium diisopropylamide. The resulting anion is quenched with N-fluorodibenzene-sulfonamide (NFSI) and the ester hydrolyzed using standard conditions known in the art to give the fluorinated keto-acid 79. A second synthetic route in Scheme 6 converts ester 77 to acid chloride 80 using reaction conditions previously described, followed by coupling intermediate 80 with a compound of Formula II via Friedel-Craft reaction conditions. The resulting alpha fluoro-substituted ketone (81) is cooled to about −78° C. in a solvent such as, for example, tetrahydrofuran and the like and treated with bromomethyl acetate (82) to give the keto-ester 83. Subsequent fluorination and hydrolysis of 83 as previously described yields the alpha, beta-difluoroketo-acid (84).

Additionally, ester derivatives of a compound of Formula I, which may be useful as prodrugs, may be prepared as follows:

Anhydrides of Formulas 2–5 or 58–59 can be reacted with an alkoxide such as, for example, NaOR$^{10}$ or KOR$^{10}$ wherein R$^{10}$ is alkyl or benzyl in a solvent such as, for example, an alcohol of the Formula R$^{10}$OH wherein R$^{10}$ is a defined above, and the like to afford respectively the half acid ester derivative of succinic or maleic acid which can then be converted to the respective acid chloride by reaction with oxalyl chloride in a solvent such as, for example, dichloromethane and the like. Subsequent reaction of the acid chloride with a compound of Formula II using Friedel-Craft acylation conditions described in Schemes 1 and 3 affords the ester derivatives of a compound of Formula I.

Compounds of Formula II, 2–5, 54, 56, 58, 59, 63, and 77 are either known in the art or can be readily prepared by a skilled artisan.

Scheme 1

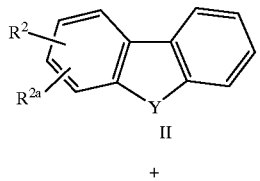

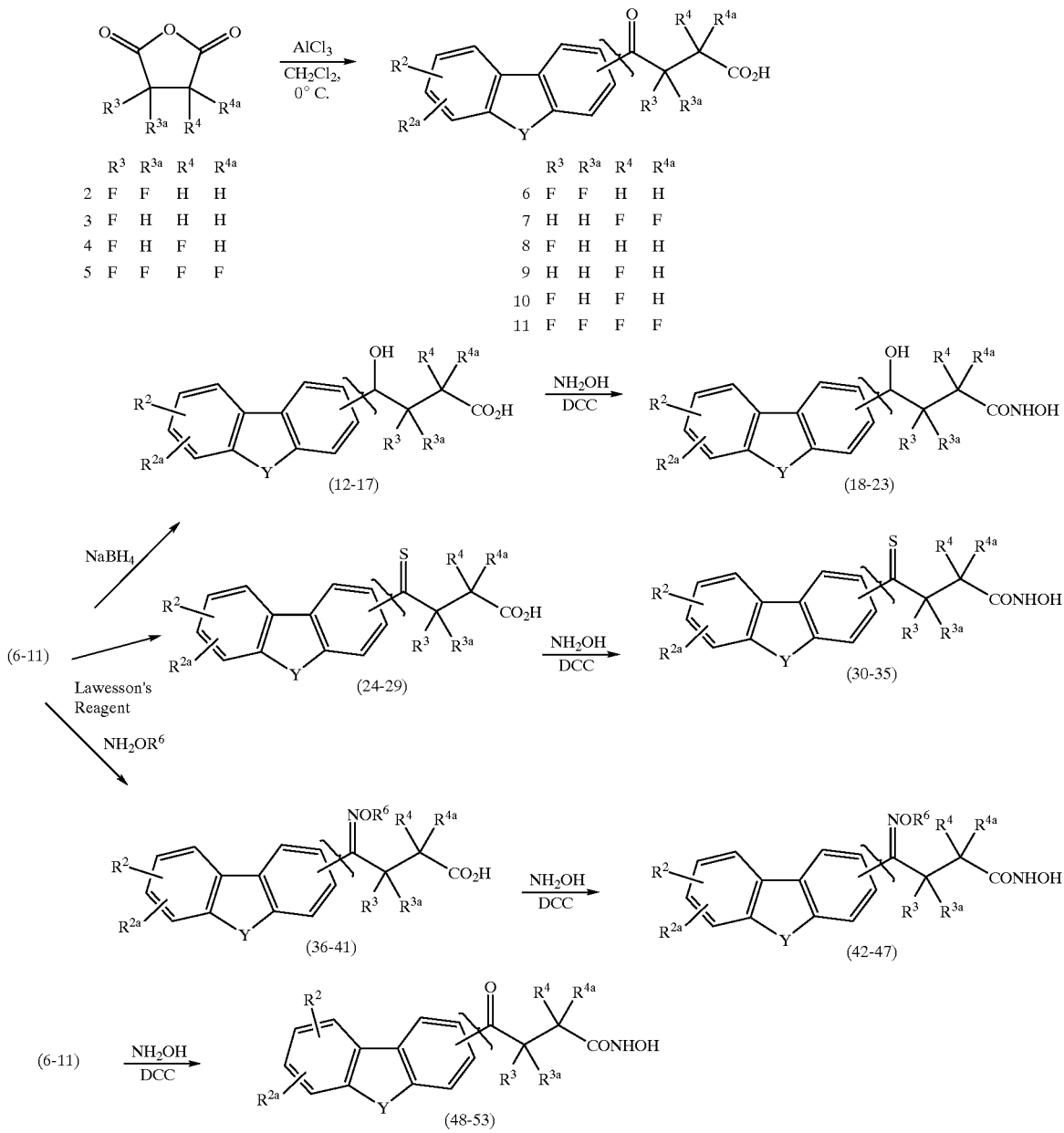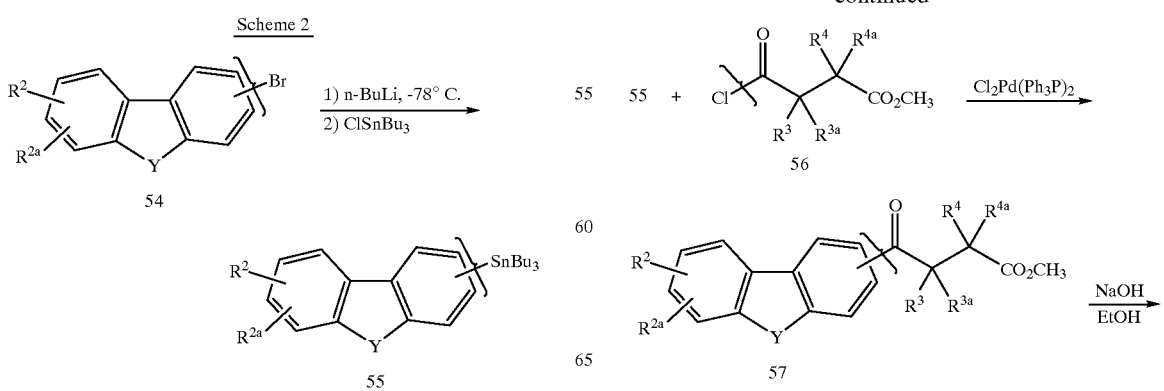

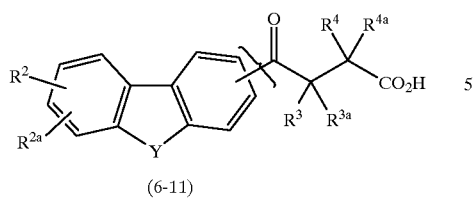
(6-11)
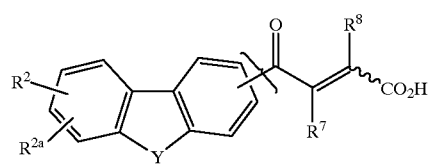
60 $R^7 = F, R^8 = H$
61 $R^7 = H, R^8 = F$
62 $R^7 = F, R^8 = F$
Scheme 3
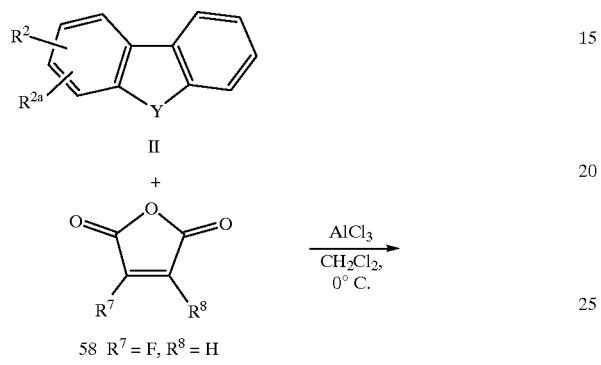
58 $R^7 = F, R^8 = H$
59 $R^7 = F, R^8 = F$
Scheme 4

-continued
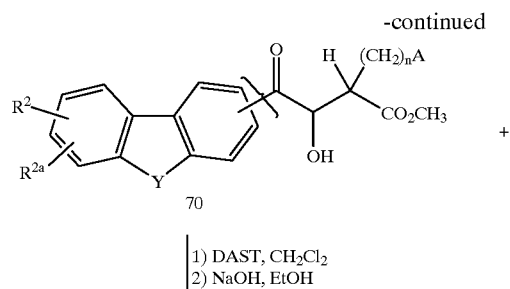
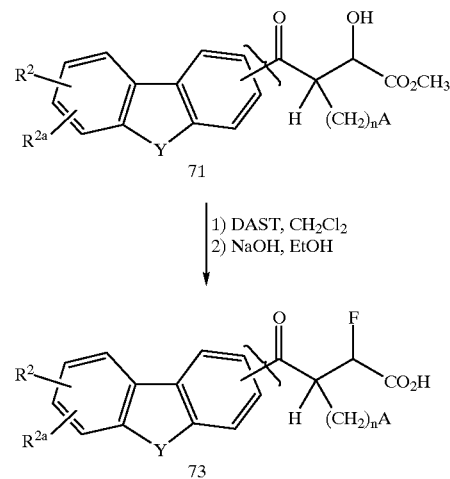
A = aryl, heteroaryl, or phthalimido
Scheme 5
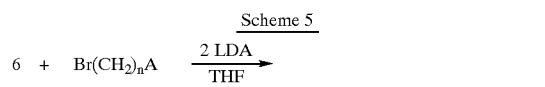
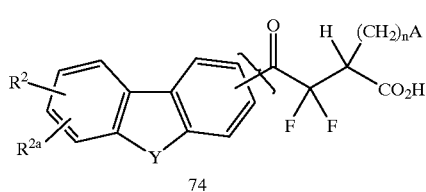
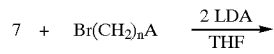
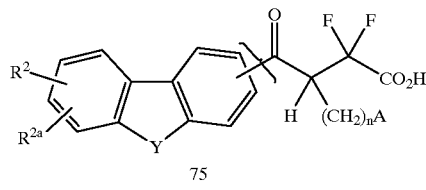
A = aryl, heteroaryl, or phthalimido
Scheme 6
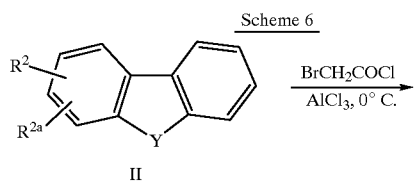
-continued
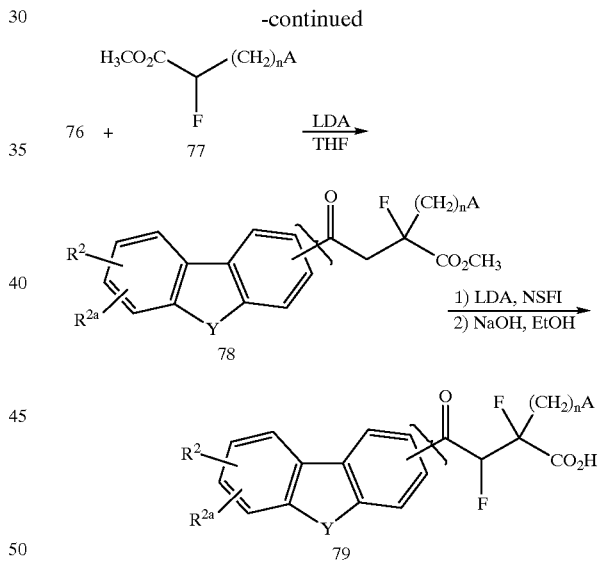
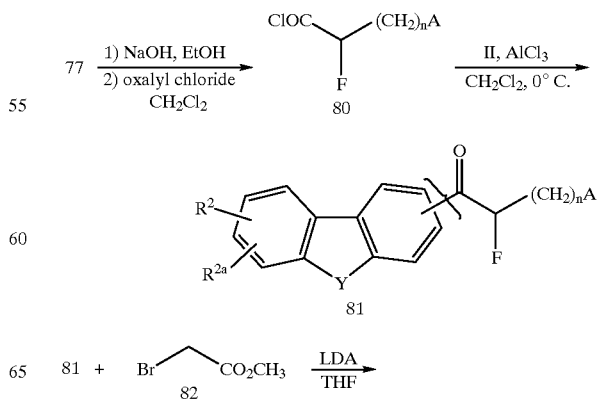

-continued

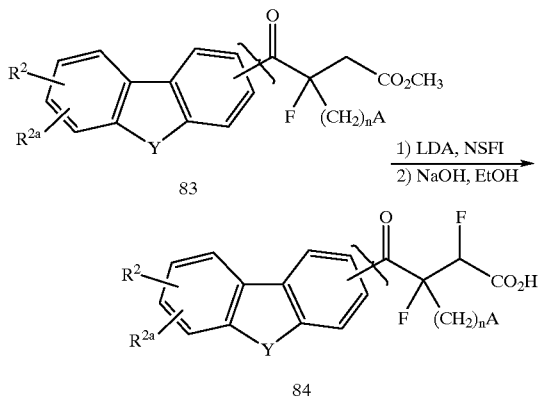

A = aryl, heteroaryl, or phthalimido

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. It will be obvious to those skilled in the art that the following dosage forms may comprise as the active component, either a compound of Formula I or a corresponding pharmaceutically acceptable salt of a compound of Formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from 5 or 10 to about 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component, with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizing, and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 1 mg to 1000 mg, preferably 10 mg to 100 mg according to the particular application and the potency of the active component. The composition can, if desired, also contain other compatible therapeutic agents.

In therapeutic use as agents for the treatment of multiple sclerosis, atherosclerotic plaque rupture, aortic aneurism, heart failure, restenosis, periodontal disease, corneal ulceration, treatment of burns, decubital ulcers, wound healing, cancer, inflammation, pain, arthritis, or other autoimmune or inflammatory disorders dependent upon tissue invasion by leukocytes, or other activated migrating cells, acute and chronic neurodegenerative disorders including stroke, head trauma, spinal cord injury, Alzheimer's disease, amyotrophic lateral sclerosis, cerebral amyloid angiopathy, AIDS, Parkinson's disease, Huntington's disease, prion diseases, myasthenia gravis, and Duchenne's muscular dystrophy. The compounds utilized in the pharmaceutical methods of the invention are administered at the initial dosage of about 1 mg to about 100 mg per kilogram daily. A daily dose range of about 25 mg to about 75 mg per kilogram is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstance is reached. For convenience, the total daily dosage may be divided and administered in portions during the day if desired.

The following nonlimiting examples illustrate the inventors' preferred methods for preparing the compounds of the invention.

EXAMPLE 1

4-Dibenzofuran-2-yl-3,3-difluoro-4-oxo-butyric acid

To a suspension of aluminum chloride (3 g, 0.022 mol) in dichloromethane (45 mL) cooled to 0° C. was added a mixture of dibenzofuran (3 g, 0.018 mol) and 2,2-difluorosuccinic anhydride (2.5 g, 0.018 mol) at such a rate so as to maintain a reaction temperature of 0° C. The reaction mixture was stirred at 0° C. for 3 hours, then poured over ice. The mixture was diluted with acetone/ethyl acetate (1:1, 100 mL), the layers were separated, and the organic phase was dried (magnesium sulfate ($MgSO_4$)), filtered, and the filtrate was concentrated in vacuo leaving a viscous brown liquid. The liquid was diluted with ethyl acetate/acetone (1:1) and passed through a silica gel column (elution with ethyl acetate/acetone (1:1)) to give unreacted dibenzofuran (0.4 g) and two major products. Fractions containing the faster eluting product ($R_f$=0.4) were combined and concentrated to dryness to give 0.32 g of the title compound as a white solid; mp 148–150° C.; Proton Nuclear Magnetic Resonance Spectroscopy ($^1$HNMR): δ 8.8 (s, 1H), 8.3 (d, 1H), 8.1 (d, 1H), 7.8 (d, 1H), 7.7 (d, 1H), 7.5 (t, 1H), 7.4 (t, 1H), 3.4 (t, 2H) ppm; Chemical Ionization Mass Spectroscopy (CI-MS) $[M+H]^+$ 305.

EXAMPLE 2

4-Dibenzofuran-2-yl-2,2-difluoro-4-oxo-butric acid

Chromatographic fractions from Example 1 containing the slower eluting product ($R_f$=0.2) were combined and concentrated in vacuo to give 0.4 g of the title compound as a yellow solid; mp 158–160° C. dec; $^1$HNMR: δ 8.9 (s, 1H), 8.2 (d, 1H), 8.1 (d, 1H), 7.8 (d, 1H), 7.7 (d, 1H), 7.5 (t, 1H), 7.4 (t, 1H), 4.3 (t, 2H) ppm; CI-MS $[M+H]^+$ 305.

In a process analogous to Examples 1 and 2 using 7-bromodibenzofuran, 8-hydroxydibenzofuran, and 7-bromofluorene in place of dibenzofuran, respectively, the following compounds (Examples 3–5) of Formula I may be prepared:

EXAMPLE 3

4-(7-Bromo-dibenzofuran-2-yl)-3,3-difluoro-4-oxo-butyric acid

EXAMPLE 4

3,3-Difluoro-4-(8-hydroxy-dibenzofuran-2-yl)-4-oxo-butyric acid

EXAMPLE 5

4-(7-Bromo-9H-fluoren-3-yl)-2,2-difluoro-4-oxo-butyric acid

In a process analogous to Example 1 using 2,3-difluorosuccinc anhydride, 2-fluorosuccinic anhydride, and 2,2,3,3-tetrafluorosuccinic anhydride in place of 2,2-difluorosuccinic anhydride, and coupled with dibenzofuran, 7-nitrodibenzofuran, and dibenzothiophene, respectively, using the Friedel-Craft conditions described, the corresponding compounds (Examples 6–10) of Formula I may be prepared:

EXAMPLE 6

4-Dibenzofuran-2-yl-2,3-difluoro-4-oxo-butyric acid

EXAMPLE 7

4-Dibenzofuran-2-yl-2-fluoro-4-oxo-butyric acid

EXAMPLE 8

3-Fluoro-4-(7-nitrodibenzofuran-2-yl)-4-oxo-butyric acid

EXAMPLE 9

4-Dibenzothiophen-2-yl-2,2,3,3-tetrafluoro-4-oxo-butyric acid

EXAMPLE 10

4-Dibenzothiophen-2-yl-3-fluoro-4-oxo-butyric acid

Compounds of Formula I containing an unsaturated side chain may be prepared using the Friedel-Craft reaction conditions in a process analogous to Example 1. Thus, by replacing 2,2-difluorosuccinic anhydride in Example 1 with 2-fluoromaleic anhydride or 2,3-difluoromaleic anhydride and coupling these acylating agents with dibenzofuran or dibenzothiophene, the following compounds (Examples 11–13) may be obtained:

EXAMPLE 11

4-Dibenzofuran-2-yl-3-fluoro-4-oxo-but-2-enoic acid

EXAMPLE 12

4-Dibenzothiophen-2-yl-2,3-difluoro-4-oxo-but-2-enoic acid

EXAMPLE 13

4-Dibenzofuran-2-yl-3,3-difluoro-4-hydroxyimino-butyric acid

A solution of 4-dibenzofuran-2-yl-3,3-difluoro-4-oxo-butyric acid (1 equivalent, Example 1) and sodium acetate (1.2 equivalents) in methanol is treated with a solution of hydroxylamine hydrochloride (1.2 equivalents) in water. The solution is heated to reflux for 3 hours, then cooled, concentrated, and filtered. The filter cake is washed with water and dried in vacuo. The crude product is recrystallized from an organic solvent, such as ethyl acetate, to give the title compound.

In a process analogous to Example 13 using appropriate starting materials, the corresponding compounds of Formula I (Examples 14 and 15) may be prepared:

EXAMPLE 14

4-Dibenzofuran-2-yl-2,2-difluoro-4-hydroxyimino-butyric acid

EXAMPLE 15

4-(9H-Fluoren-3-yl)-2,2-difluoro-4-hydroxyimino-butyric acid

In a process analogous to Example 13 and substituting O-methylhydroxylamine hydrochloride for hydroxylamine hydrochloride, the corresponding compound of Formula I (Example 16) may be prepared:

EXAMPLE 16

3-Fluoro-4-methoxyimino-4-(7-nitro-dibenzofuran-2-yl)-butyric acid

EXAMPLE 17

4-Dibenzofuran-2-yl-3,3-difluoro-N-hydroxy-4-oxo-butyramide

To a solution of 4-dibenzofuran-2-yl-3,3-difluoro-4-oxo-butyric acid (1 equivalent, Example 1) in dichloromethane is added one equivalent of O-benzylhydroxylamine. The solution is cooled to 0° C. followed by the addition of dicyclohexylcarbodiimide (1 equivalent) in one portion. The reaction mixture gradually warms to room temperature and is stirred overnight. The suspension is filtered, and the filtrate is concentrated in vacuo to give the corresponding hydroxamate derivative. This crude product is taken up in absolute ethanol and is hydrogenated using 10% Palladium on carbon under a hydrogen atmosphere at 50 psi to give the title hydroxamic acid derivative.

In a process analogous to Example 17 and substituting 4-(9H-fluoren-2-yl)-2,3-difluoro-4-oxo-butyric acid for 4-dibenzofuran-2-yl-3,3-difluoro-4-oxo-butyric acid, the corresponding compound of Formula I (Example 18) may be prepared:

EXAMPLE 18

4-(9H-Fluoren-2-yl)-2,3-difluoro-N-hydroxy-4-oxo-butyramide

EXAMPLE 19

4-Dibenzofuran-2-yl-3,3-difluoro-4-hydroxy-butyric acid

A solution of 4-dibenzofuran-2-yl-3,3-difluoro-4-oxo-butyric acid (1 equivalent, Example 1) in tetrahydrofuran is added dropwise to a suspension of sodium borohydride (2 equivalents) in tetrahydrofuran cooled to 0° C. The reaction mixture gradually warms to room temperature and is stirred overnight. Excess sodium borohydride is then quenched with aqueous HCl (1 M) and further diluted with ethyl acetate. The layers are separated, and the organic portion is washed with brine, dried (MgSO$_4$), and concentrated in vacuo to give the title 4-hydroxy derivative.

EXAMPLE 20

4-Dibenzofuran-2-yl-3,3-difluoro-4-thiooxo-butyric acid

A solution of 4-dibenzofuran-2-yl-3,3-difluoro-4-oxo-butyric acid (1 equivalent, Example 1) in tetrahydrofuran is cooled to 0° C. and treated with Lawesson's reagent (2 equivalents) in one portion. The reaction mixture is allowed to gradually warm to room temperature, then refluxed for 6 hours. The solution is cooled and concentrated in vacuo. The residue is taken up in dichloromethane and purified using silica gel chromatography to give the title thioketone derivative.

EXAMPLE 21

2-(2-Dibenzofuran-2-yl-1,1-difluoro-2-oxo-ethyl)-5-(1,3-dioxo-1,3-dihydro-isoindol-2-yl)-pentanoic acid To a solution of 4-dibenzofuran-2-yl-3,3-difluoro-4-oxo-butyric acid (1 equivalent, Example 1) in tetrahydrofuran cooled to −78° C. is added dropwise two equivalents of lithium diisopropylamide. The solution is stirred for 30 minutes at −78° C. followed by the dropwise addition of a solution of N-(3-bromopropyl)phthalimide (1 equivalent) in tetrahydrofuran. The reaction mixture gradually warms to 0° C., at which time aqueous hydrochloric acid (HCl) (1 M) is added. The product is partitioned between ethyl acetate and water, the layers separated, and the organic portion is washed with brine, dried (MgSO$_4$), and concentrated in vacuo. The crude product is purified using silica gel chromatography (elution with chloroform/methanol) to afford the title compound.

In a process analogous to Example 21 and substituting benzyl bromide for N-(3-bromopropyl)-phthalimide, the corresponding compound of Formula I (Example 22) may be prepared:

EXAMPLE 22

2-Benzyl-4-dibenzofuran-2-yl-3,3-difluoro-4-oxo-butyric acid

EXAMPLE 23

3-Fluoro-4-(9-methyl-9H-carbazol-2-yl)-4-oxo-butyric acid

A solution of 2-bromo-9-methylcarbazole (1 equivalent) in tetrahydrofuran is cooled to −78° C. and carefully treated with n-butyllithium (1.15 equivalents). After stirring for 1 hour, the mixture is treated with chlorotrimethyltin. After an additional 30 minutes, the solution is gradually allowed to warm to room temperature and is concentrated in vacuo. The crude product is taken up in dichloromethane and washed successively with water and brine. The organic phase is dried (MgSO$_4$), filtered, and concentrated. Purification by silica gel chromatography (elution with hexane/ethyl acetate) gives the aryltin derivative.

To a suspension of the 2-substituted trimethyltincarbazole (1 equivalent) and bis(triphenylphosphine)-palladium (II) chloride (5 mol %) in tetrahydrofuran at −20° C. is added dropwise methyl-(2-fluoro)-succinyl chloride (1.1 equivalents). The reaction mixture gradually warms to room temperature and is refluxed for 4 hours. The mixture is cooled to room temperature and diluted with aqueous HCl (1 M) and ethyl acetate. The layers are separated, and the organic portion is washed with brine, dried (MgSO$_4$), and concentrated. The crude product obtained is purified using silica gel chromatography (elution with hexane/ethyl acetate) to give the title compound as the methyl ester.

The ester (1 equivalent) is taken up in ethanol and treated with sodium hydroxide pellets (2 equivalents) in one portion. The reaction mixture is stirred at room temperature for 4 hours, then concentrated in vacuo. The residue is taken up in water and acidified (pH=1) using concentrated HCl. Ethyl acetate is added, the layers separated, and the organic phase is dried (MgSO$_4$), filtered, and concentrated in vacuo. The crude acid is purified using silica gel chromatography (elution with chloroform/methanol) to give the title compound.

In a process analogous to Example 23 and substituting 2-bromofluorene for 2-bromo-9-methylcarbazole and methyl-(2,3-difluoro)-succinyl chloride for methyl-(2-fluoro)-succinyl chloride, the corresponding compound of Formula I (Example 24) may be prepared:

EXAMPLE 24

4-(9H-Fluoren-2-yl)-3,3-difluoro-4-oxo-butyric acid

EXAMPLE 25

4-Dibenzofuran-2-yl-2,3-difluoro-4-oxo-2-phenethyl-butyric acid

To a solution of 4-dibenzofuran-2-yl-2,3-difluoro-4-oxo-butyric acid (1 equivalent, Example 6) in tetrahydrofuran cooled to −78° C. is added dropwise a solution of lithium diisopropylamide (2 equivalents). After stirring at −78° C. for 30 minutes, a solution of phenethyl bromide (1 equivalent) in tetrahydrofuran is added. The cooling bath is removed, and the reaction mixture gradually warms to room temperature and is stirred overnight. To this solution is added aqueous HCl (1 M) and ethyl acetate. The layers are separated, and the organic portion is washed with brine, dried (MgSO$_4$), and concentrated in vacuo. The title compound is obtained by separation from the reaction by-product using silica gel chromatography (elution with chloroform/methanol).

We claim:
1. A compound of Formula I

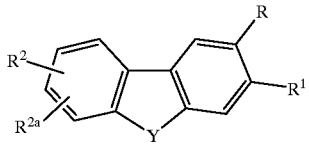

wherein one of R or $R^1$ is hydrogen and the other is

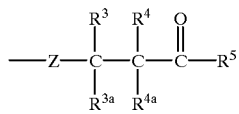

wherein

Z is 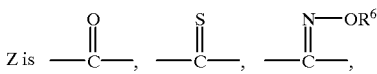

wherein $R^6$ is hydrogen,
 alkyl,
 —$(CH_2)_n$-aryl wherein n is zero or an integer of 1 to 5, or
 —$(CH_2)_n$-cycloalkyl wherein n is as defined above, or

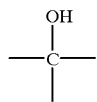

$R^3$, $R_{3a}$, $R^4$, and $R^{4a}$ are independently the same or different and are hydrogen,
 fluorine,
 alkyl,
 —$(CH_2)_n$-aryl wherein n is as defined above,
 —$(CH_2)_n$—N-phthalimido wherein n is as defined above, or
 —$(CH_2)_n$-heteroaryl wherein n is as defined above, and $R^5$ is OH or
 NH—OH, or

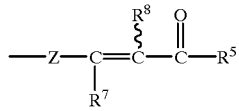

wherein $R^7$ and $R^8$ are independently the same or different and are hydrogen or fluorine and Z and $R^5$ are as defined above;

$R^2$ is hydrogen,
 alkyl,
 alkoxy,
 halogen,
 hydroxy,
 cyano,
 nitro,
 trifluoromethyl,

—$CO_2R^9$ wherein $R^9$ is hydrogen or alkyl,
—$COR^9$ wherein $R^9$ is as defined above,
—$SO_3R^9$ wherein $R^9$ is as defined above,

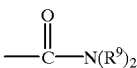

wherein $R^9$ is as defined above, or
 —$(CH_2)_nN(R^9)_2$ wherein n and $R^9$ are as defined above;

$R^{2a}$ is hydrogen,
 alkyl,
 alkoxy,
 halogen,
 hydroxy, or
 cyano; and

Y is

wherein $R^9$ is as defined above,
 —O—,
 —$S(O)_m$— wherein m is zero or an integer of 1 or 2,

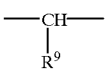

wherein $R^9$ is as defined above,

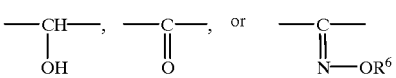

wherein $R^6$ is as defined above;

with the proviso that at least one of $R^3$, $R^{3a}$, $R^4$, or $R^{4a}$ is fluorine and at least one of $R^7$ and $R^8$ is fluorine;

and corresponding isomers thereof; a pharmaceutically acceptable prodrug thereof; or a pharmaceutically acceptable salt thereof.

2. A compound according to claim 1 wherein R is

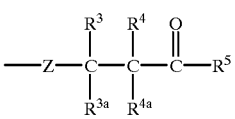

wherein

Z is 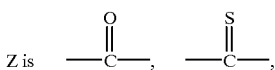

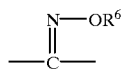

wherein
R⁶ is hydrogen,
alkyl,
—(CH₂)ₙ-aryl wherein n is zero or an integer of 1 to 5, or
—(CH₂)ₙ-cycloalkyl wherein n is as defined above, or

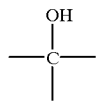

R³, R³ᵃ, R⁴, and R⁴ᵃ are independently the same or different and are hydrogen,
fluorine,
alkyl,
—(CH₂)ₙ-aryl wherein n is as defined above,
—(CH₂)ₙ—N-phthalimido wherein n is as defined above, or
—(CH₂)ₙ-heteroaryl wherein n is as defined above, and
R⁵ is OH or
NH—OH, or

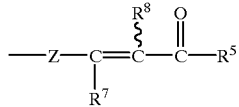

wherein
R⁷ and R⁸ are independently the same or different and are hydrogen or fluorine and Z and R⁵ are as defined above;
R¹ is hydrogen; and
Y is —O—, or
—CH₂—.

3. A compound according to claim 2 wherein R¹, R², and R²ᵃ are hydrogen.

4. A compound according to claim 3 wherein

R is 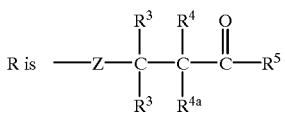

wherein
Z is

R³ and R³ᵃ are hydrogen or fluorine,
R⁴ and R⁴ᵃ are hydrogen,

—(CH₂)ₙ-aryl wherein n is zero or an integer of 1 to 5,
—(CH₂)ₙ—N-phthalimido wherein n is as defined above, or
—(CH₂)ₙ-heteroaryl wherein n is as defined above, and
R⁵ is OH or
NH—OH.

5. A compound according to claim 4 wherein R⁵ is OH.
6. A compound according to claim 5 wherein
Z is

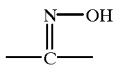

and
R⁵ is OH.

7. A compound selected from the group consisting of:
2-Benzyl-4-dibenzofuran-2-yl-3,3-difluoro-4-oxo-butyric acid;
4-Dibenzofuran-2-yl-3,3-difluoro-4-hydroxyimino-butyric acid;
4-Dibenzofuran-2-yl-3,3-difluoro-N-hydroxy-4-oxo-butyramide;
4-Dibenzofuran-2-yl-3-fluoro-4-oxo-but-2-enoic acid;
4-Dibenzofuran-2-yl-3,3-difluoro-4-thioxo-butyric acid;
4-Dibenzofuran-2-yl-3,3-difluoro-4-hydroxy-butyric acid;
4-(7-Bromo-dibenzofuran-2-yl)-3,3-difluoro-4-oxo-butyric acid;
3,3-Difluoro-4-(8-hydroxy-dibenzofuran-2-yl)-4-oxo-butyric acid;
4-Dibenzofuran-2-yl-3,3-difluoro-4-oxo-butyric acid;
4-Dibenzofuran-2-yl-2,3-difluoro-4-oxo-2-phenethyl-butyric acid;
4-Dibenzofuran-2-yl-2,2-difluoro-4-hydroxyimino-butyric acid;
3-(Dibenzofuran-2-carbonyl)-2-fluoro-5-pyridin-2-yl-pentanoic acid;
2-(2-Dibenzofuran-2-yl-1,1-difluoro-2-oxo-ethyl)-5-(1,3-dioxo-1,3-dihydro-isoindol-2-yl)-pentanoic acid;
3-Fluoro-4-methoxyimino-4-(7-nitrodibenzofuran-2-yl)-butyric acid;
4-(9H-Fluoren-2-yl)-3,3-difluoro-4-oxo-butyric acid;
4-(7-Bromo-9H-fluoren-3-yl)-2,2-difluoro-4-hydroxyimino-butyric acid;
4-(9H-Fluoren-2-yl)-2,3-difluoro-N-hydroxy-4-oxo-butyramide;
4-Dibenzothiophen-2-yl-2,2,3,3-tetrafluoro-4-oxo-butyric acid;
2-Benzyl-4-dibenzothiophen-2-yl-3-fluoro-4-oxo-butyric acid;
4-Dibenzothiophen-2-yl-2,3-difluoro-4-oxo-but-2-enoic acid;
4-(9H-Carbazol-2-yl)-2,2-difluoro-4-hydroxyimino-butyric acid;
3-Fluoro-4-(9-methyl-9H-carbazol-2-yl)-4-oxo-butyric acid;
4-Dibenzofuran-2-yl-2,2-difluoro-4-oxo-butyric acid;
4-(7-Bromo-9H-fluoren-3-yl)-2,2-difluoro-4-oxo-butyric acid;
4-Dibenzofuran-2-yl-2,3-difluoro-4-oxo-butyric acid;

4-Dibenzofuran-2-yl-2-fluoro-4-oxo-butyric acid;

3-Fluoro-4-(7-nitrodibenzofuran-2-yl)-butyric acid;

4-Dibenzothiophen-2-yl-3-fluoro-4-oxo-butyric acid; and 4-(9H-Fluoren-3-yl)-2,2-difluoro-4-hydroxyimino-butyric acid; and corresponding isomers thereof; a pharmaceutically acceptable prodrug thereof; or a pharmaceutically acceptable salt thereof.

8. A compound which is 4-dibenzofuran-2-yl-2,2-difluoro-4-oxo-butyric acid; a pharmaceutically acceptable prodrug thereof; or a pharmaceutically acceptable salt thereof.

9. A compound which is 4-dibenzofuran-2-yl-3,3-difluoro-4-oxo-butyric acid; a pharmaceutically acceptable prodrug thereof; or a pharmaceutically acceptable salt thereof.

10. A method of inhibiting a matrix metalloproteinase comprising administering to a host suffering therefrom a therapeutically effective amount of a compound according to claim 1 in unit dosage form.

11. A method of inhibiting gelatinase A comprising administering to a host suffering therefrom a therapeutically effective amount of a compound according to claim 1 in unit dosage form.

12. A method of inhibiting stromelysin-1 comprising administering to a host suffering therefrom a therapeutically effective amount of a compound according to claim 1 in unit dosage form.

13. A method of inhibiting collagenase comprising administering to a host suffering therefrom a therapeutically effective amount of a compound according to claim 1 in unit dosage form.

14. A method of inhibiting matrilysin comprising administering to a host suffering therefrom a therapeutically effective amount of a compound according to claim 1 in unit dosage form.

15. A method of inhibiting MMP-13 comprising administering to a host suffering therefrom a therapeutically effective amount of a compound according to claim 1 in unit dosage form.

16. A method of preventing atherosclerotic plaque rupture comprising administering to a host suffering therefrom a therapeutically effective amount of a compound according to claim 1 in unit dosage form.

17. A method of inhibiting aortic aneurism comprising administering to a host suffering therefrom a therapeutically effective amount of a compound according to claim 1 in unit dosage form.

18. A method of inhibiting heart failure comprising administering to a host suffering therefrom a therapeutically effective amount of a compound according to claim 1 in unit dosage form.

19. A method of preventing restenosis comprising administering to a host suffering therefrom a therapeutically effective amount of a compound according to claim 1 in unit dosage form.

20. A method of controlling periodontal disease comprising administering to a host suffering therefrom a therapeutically effective amount of a compound according to claim 1 in unit dosage form.

21. A method of treating corneal ulceration comprising administering to a host suffering therefrom a therapeutically effective amount of a compound according to claim 1 in unit dosage form.

22. A method of treating burns comprising administering to a host suffering therefrom a therapeutically effective amount of a compound according to claim 1 in unit dosage form.

23. A method of treating decubital ulcers comprising administering to a host suffering therefrom a therapeutically effective amount of a compound according to claim 1 in unit dosage form.

24. A method of treatment for healing wounds comprising administering to a host suffering therefrom a therapeutically effective amount of a compound according to claim 1 in unit dosage form.

25. A method of treating cancer comprising administering to a host suffering therefrom a therapeutically effective amount of a compound according to claim 1 in unit dosage form.

26. A method of treating arthritis comprising administering to a host suffering therefrom a therapeutically effective amount of a compound according to claim 1 in unit dosage form.

27. A method of treating autoimmune or inflammatory disorders dependent upon tissue invasion by leukocytes comprising administering to a host suffering therefrom a therapeutically effective amount of a compound according to claim 1 in unit dosage form.

28. A method of treating multiple sclerosis comprising administering to a host suffering therefrom a therapeutically effective amount of a compound according to claim 1 in unit dosage form.

29. A method of treating inflammation and pain comprising administering to a host suffering therefrom a therapeutically effective amount of a compound according to claim 1 in unit dosage form.

30. A method of treating acute and chronic neurodegenerative disorders selected from the group consisting of: stroke, head trauma, spinal cord injury, Alzheimer's disease, amyotrophic lateral sclerosis, cerebral amyloid angiopathy, AIDS, Parkinson's disease, Huntington's diseases, prion diseases, myasthenia gravis, and Duchenne's muscular dystrophy comprising administering to a host suffering therefrom a therapeutically effective amount of a compound according to claim 1 in unit dosage form.

31. A pharmaceutical composition comprising a compound according to claim 1 in admixture with a pharmaceutically acceptable excipient, diluent, or carrier.

32. A pharmaceutical composition comprising a therapeutically effective amount of a compound according to claim 1 in admixture with a pharmaceutically acceptable excipient, diluent, or carrier.

* * * * *